US012806344B2

(12) United States Patent
Mulcahy

(10) Patent No.: US 12,806,344 B2
(45) Date of Patent: Nov. 24, 2026

(54) APPARATUS, SYSTEM, AND METHOD FOR DELIVERING AND TRACKING AN INJECTABLE DELIVERABLE

(71) Applicant: JABIL INC., St. Petersburg, FL (US)

(72) Inventor: Thomas Conor Mulcahy, St. Petersburg, FL (US)

(73) Assignee: JABIL INC.

(*) Notice: Subject to any disclaimer, the term of this patent is extended or adjusted under 35 U.S.C. 154(b) by 302 days.

(21) Appl. No.: 17/484,041

(22) Filed: Sep. 24, 2021

(65) Prior Publication Data

US 2022/0118193 A1 Apr. 21, 2022

Related U.S. Application Data

(60) Provisional application No. 63/082,959, filed on Sep. 24, 2020.

(51) Int. Cl.

| | |
|---|---|
| ***A61M 5/315*** | (2006.01) |
| ***G16H 20/17*** | (2018.01) |
| ***H04W 4/80*** | (2018.01) |

(52) U.S. Cl.

CPC .... *A61M 5/31568* (2013.01); *A61M 5/31538* (2013.01); *A61M 5/3157* (2013.01); *A61M 5/31571* (2013.01); *G16H 20/17* (2018.01); *H04W 4/80* (2018.02)

(58) Field of Classification Search

CPC ............ A61M 5/31568; A61M 5/3157; A61M 5/31571; G16H 20/17; H04W 4/80

See application file for complete search history.

(56) References Cited

U.S. PATENT DOCUMENTS

| | | | | |
|---|---|---|---|---|
| 9,152,829 | B2 * | 10/2015 | Day | A61M 15/0083 |
| 10,350,357 | B2 * | 7/2019 | Park | A61M 5/20 |
| 10,463,787 | B2 * | 11/2019 | Shor | A61M 5/31528 |
| 2013/0245545 | A1 * | 9/2013 | Arnold | A61M 5/1723 604/66 |
| 2020/0261654 | A1 * | 8/2020 | Kühni | A61M 5/20 |
| 2021/0327561 | A1 * | 10/2021 | Schabbach | A61B 5/4839 |

FOREIGN PATENT DOCUMENTS

| | | | | |
|---|---|---|---|---|
| WO | WO-2006084464 | A1 * | 8/2006 | G16H 20/17 |

* cited by examiner

*Primary Examiner* — Laura A Bouchelle

(74) *Attorney, Agent, or Firm* — Riverside Law LLP

(57) ABSTRACT

Apparatuses, systems and methods of providing an injectable medication delivery system. The embodiments may include a powered mobile injector pen capable of receiving a cartridge having a deliverable therein, and of delivering the deliverable to a patient; a base station suitable to receive communications from, and to provide an electrical charge to, the powered injector pen, and comprising a communications gateway; and a remote communications hub capable of exchanging wireless communications with the communications gateway.

17 Claims, 10 Drawing Sheets

APPARATUS, SYSTEM, AND METHOD FOR DELIVERING AND TRACKING AN INJECTABLE DELIVERABLE

CROSS-REFERENCE TO RELATED APPLICATIONS

The present application claims benefit of priority to U.S. Provisional Application No. 63/082,959, filed Sep. 24, 2020, entitled: "Apparatus, System and Method for Delivering and Tracking an Injectable Deliverable," the entirety of which is incorporated herein by reference as if set forth in its entirety.

BACKGROUND

Field of the Disclosure

Embodiments disclosed herein relate to patient health, and, more particularly, to an apparatus, system and method for delivering and tracking an injectable deliverable.

Description of the Background

In an at-home medication regimen, successful treatment necessitates both adherence and compliance. Compliance is defined as proper administration of the medication, including the delivery thereof. Adherence is defined as the routine of taking treatment per the prescribed frequency, i.e., at the correct time of day and/or the proper number of times per day.

Taking medication as prescribed and for the recommended time period is problematic for many patients, and can have significant effects on health care outcomes, efficacy of treatments, and cost of care. For persons with chronic disorders, it has been estimated that as many as 60% of patients are poorly adherent to their prescribed medication.

Most patients indicate that the first several treatments are critical to ensure long term compliance. Patients indicate confusion during early treatments as to difficulties in the use of the injector, loading of the injector, and so on, and that this confusion can have a drastic effect on long term compliance. Further, even longer-term patients frequently express concern over modifications in protocols, injector pens, dosing instructions, drug recalls, and the like, and these concerns also have a drastic effect on protocol compliance.

It would therefore be desirable to provide apparatuses, systems and methods to better deliver and track the delivery of and need for an injectable deliverable, such as medication.

SUMMARY

Disclosed are exemplary apparatuses, systems and methods of providing an injectable medication delivery system. The embodiments may include a powered mobile injector pen capable of receiving a cartridge having a deliverable therein, and of delivering the deliverable to a patient; a base station suitable to receive communications from, and to provide an electrical charge to, the powered injector pen, and comprising a communications gateway; and a remote communications hub capable of exchanging wireless communications with the communications gateway.

Therefore, the embodiments provide apparatuses, systems and methods to better deliver and track the delivery of and need for an injectable deliverable, such as medication.

BRIEF DESCRIPTION OF THE DRAWINGS

The disclosure is provided using the text herein, as well as the accompanying drawings, in which like numerals may represent like elements, and in which.

DETAILED DESCRIPTION

Figure 1A:
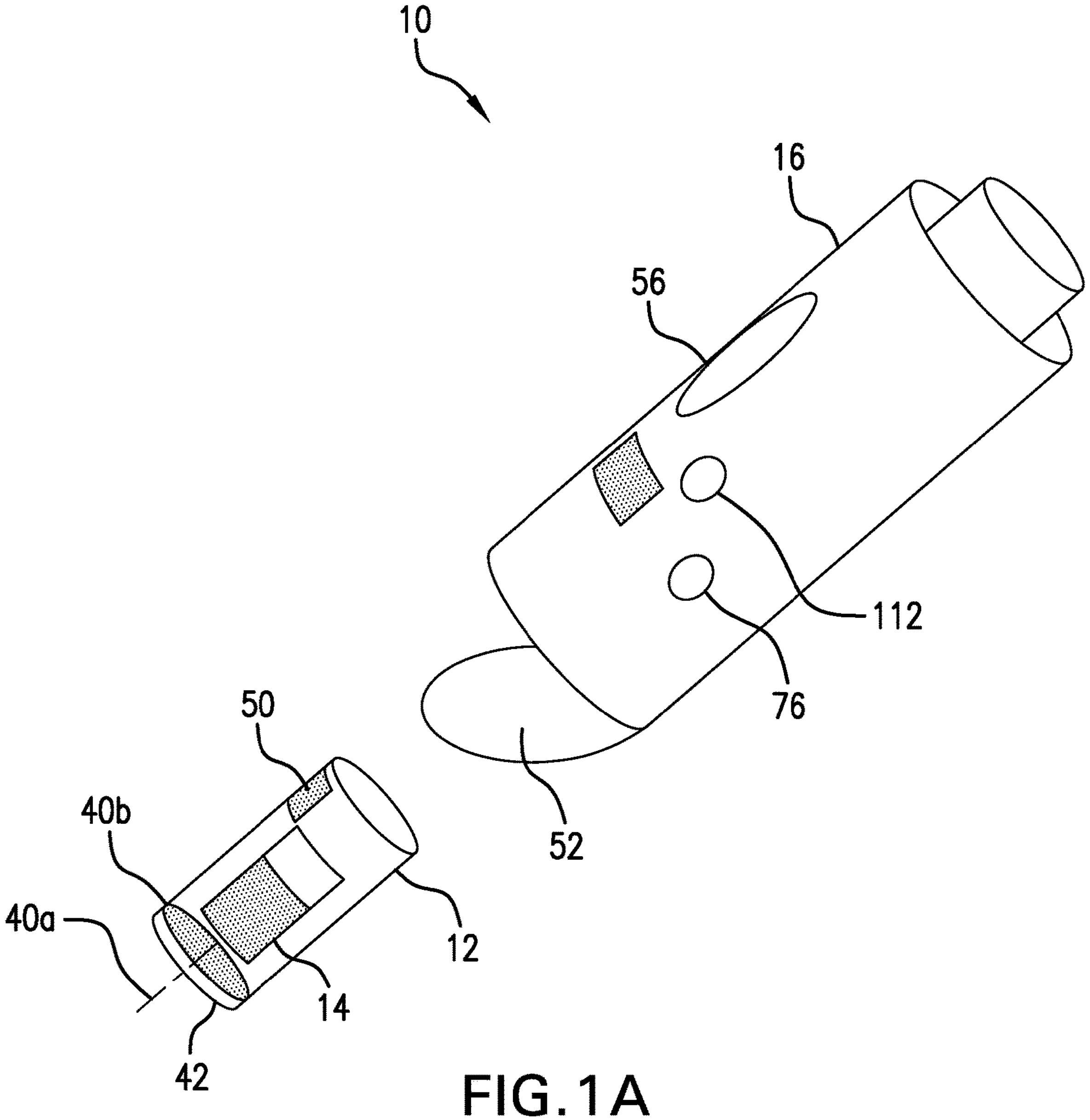
FIG. 1*a* is an illustration of aspects of the embodiments.

The figures and descriptions provided herein may have been simplified to illustrate aspects that are relevant for a clear understanding of the herein described devices, systems, and methods, while eliminating, for the purpose of clarity, other aspects that may be found in typical similar devices, systems, and methods. Those of ordinary skill may recognize that other elements and/or operations may be desirable and/or necessary to implement the devices, systems, and methods described herein. But because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that embodiments may be embodied in different forms. As such, the embodiments should not be construed to limit the scope of the disclosure.

The terminology used herein is for the purpose of describing particular example embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another element, component, region, layer or section. That is, terms such as "first," "second," and other numerical terms, when used herein, do not imply a sequence or order unless clearly indicated by the context. Thus, a first element, component, region, layer or section discussed below could be termed a second element, component, region, layer or section without departing from the teachings of the exemplary embodiments.

Processor-implemented modules and print systems are disclosed herein that may provide access to and transformation of a plurality of types of digital content, including but not limited to tracking algorithms, triggers, and data streams, and the particular algorithms applied herein may track, deliver, manipulate, transform, transceive and report the accessed data. Described embodiments of the modules, apps, systems and methods that apply these particular algorithms are thus intended to be exemplary and not limiting.

An exemplary computing processing system for use in association with the embodiments, by way of non-limiting example, is capable of executing software, such as an operating system (OS), applications/apps, user interfaces, and/or one or more other computing algorithms, such as the tracking, algorithms, decisions, models, programs and subprograms discussed herein. The operation of the exemplary processing system is controlled primarily by non-transitory computer readable instructions/code, such as instructions stored in a computer readable storage medium, such as hard disk drive (HDD), optical disk, solid state drive, or the like. Such instructions may be executed within the central processing unit (CPU) to cause the system to perform the disclosed operations. In many known computer servers, workstations, mobile devices, personal computers, and the like, the CPU is implemented in an integrated circuit called a processor.

It is appreciated that, although the exemplary processing system may comprise a single CPU, such description is merely illustrative, as the processing system may comprise a plurality of CPUs. As such, the disclosed system may exploit the resources of remote CPUs through a communications network or some other data communications means.

In operation, CPU fetches, decodes, and executes instructions from a computer readable storage medium. Such instructions may be included in software. Information, such as computer instructions and other computer readable data, is transferred between components of the system via the system's main data-transfer path.

In addition, the processing system may contain a peripheral communications controller and bus, which is responsible for communicating instructions from CPU to, and/or receiving data from, peripherals, such as operator interaction elements, as discussed herein throughout. An example of a peripheral bus is the Peripheral Component Interconnect (PCI) bus that is well known in the pertinent art.

An operator display/graphical user interface (GUI) may be used to display visual output and/or presentation data generated by or at the request of processing system, such as responsive to operation of the aforementioned computing programs/applications. Such visual output may include text, graphics, animated graphics, and/or video, for example.

Further, the processing system may contain a network adapter which may be used to couple to an external communication network, which may include or provide access to the Internet, an intranet, an extranet, or the like. Communications network may provide access for processing system with means of communicating and transferring software and information electronically. Network adaptor may communicate to and from the network using any available wired or wireless technologies. Such technologies may include, by way of non-limiting example, cellular, Wi-Fi, Bluetooth, infrared, or the like.

The disclosure is directed to a connected reusable injector with a firing mechanism capable of firing the needle of a reloadable cassette in order to inject the deliverable. This injector pen is periodically associated with a base station that includes a communications gateway.

Figure 1B:
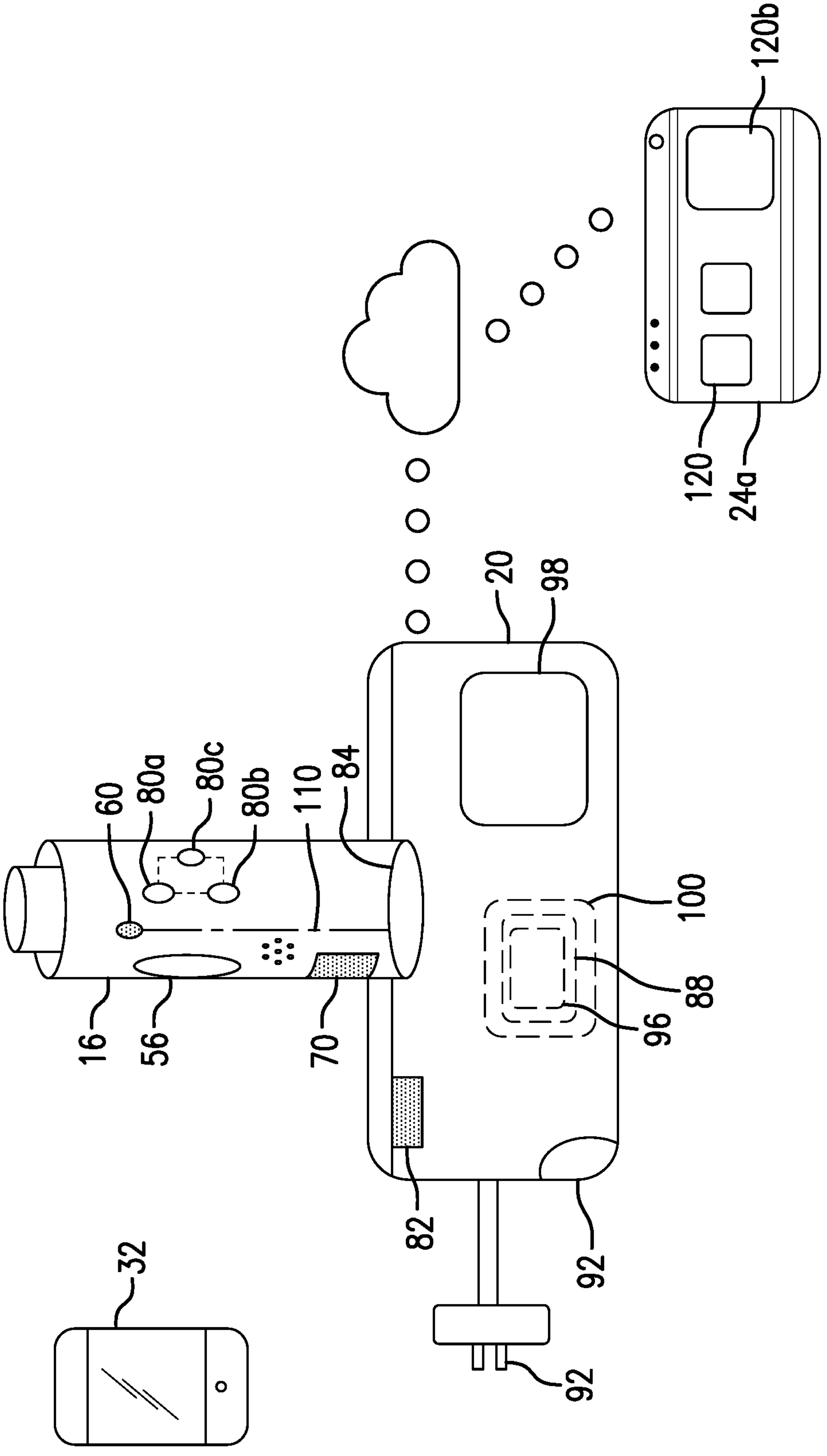
FIG. 1*b* is an illustration of aspects of the embodiments.

FIGS. 1A and 1B illustrate a medication delivery system 10 according to the embodiments. The system includes five components, namely: a medication cartridge 12; a deliverable 14, such as the medication, within the cartridge 12; a powered delivery device 16, such as an injector pen, suitable to receive the cartridge 12 and deliver the deliverable 14 therefrom; a base station 20 suitable to receive communications from, and charge, the powered delivery device 16; and a communications hub 24 in the cloud 28 capable of exchanging communications with the base station 20. The system 10 may additionally include an "app" 30, such as may operate on a mobile device 32, which is capable of communication with any or all of the powered delivery device 16, the base station 20 and/or the hub 24.

As indicated, the cartridge 12 may include, such as stored within a sealed aspect along a lateral axis thereof, the deliverable 14. The deliverable 14 may be, for example, a medicine of any type, and may preferably constitute a single dose of that medication. The cartridge 12 may additionally include a needle 40*a* or a needle interface seal 40*b*, through which the medication 14 may be delivered.

The cartridge 12 may include a safety cap 42. The safety cap 42 may protect the needle 40*a* or the needle interface seal 40*b*. As such, the safety cap 42 may protect a user/patient from being injured by the needle 40*a*, and/or may prevent leakage of the medication 14 through the needle interface seal 40*b*.

The cartridge 12 may include on or more readable identification features 50. The identification feature or features 50 may be electronically readable, such as by the injector pen 16 and/or by the base station 20. Readable identification 50 may be or include a RFID tag, a bar code, a QR code, a near field communications (NFC) tag, an electronic signature, or the like.

The powered delivery system 16 may deliver the deliverable 14, i.e., the medication, to a patient. This delivery may occur via actuation of a needle 52 associated with the injector pen 16 and gaining access to the deliverable 14 through the needle interface seal 40*b* on the cartridge 12; or delivery may occur via actuation of a firing mechanism 56 on the injector pen 16 that injects the deliverable 14 through the needle 40*a* associated with the cartridge 12.

Accordingly, the firing mechanism 56 may be associated with the injector pen 16 to fire a needle 52 on the pen 16, or may fire a needle 40*a* associated with the cartridge 12. As such, the firing mechanism 56 may be mechanical, electrical, or electro-mechanical.

The injector pen 16 may include one or more user interfaces (UI) and/or alert mechanisms (AM) 60. The UI/AM 60 may be visual, audible, or tactile, such as an LCD, LEDs, speakers, or a buzzer. The UI/AM 60 may receive user input, and/or may deliver alerts or instructions to the user/patient.

The injector pen 16 may include one or more readable identification features 64. The identification feature or features 64 may be electronically readable, such as by the base station 20. Readable identification 64 may be or include a RFID tag, a bar code, a QR code, a near field communications (NFC) tag, an electronic signature, or the like.

The injector pen 16 may include one or more electronic readers 70 capable of reading the identification features 50 on the cartridge 12, which cartridge identification features 50 are referenced above. Reading of the cartridge identification 50 may enable knowledge at the injector pen 16 of the drug type, the proper drug dosage, and the like. Moreover, this information, particularly if received by the pen 16 in conjunction with additional information from the gateway 100 at the base station 20, as discussed herein throughout, may allow for the actuation of alerts or locking mechanisms to prevent dispersal of the deliverable 14 in the event of an error.

The firing mechanism 56 of the injector pen 16 may thus include a locking mechanism 76. The locking mechanism 76 may be mechanical, electrical, or electro-mechanical, and may prevent firing of the firing mechanism 56 to dispense the deliverable 14. The locking mechanism 76 may be actuated responsive to an identification from the cartridge 12, a dosing dispersal error, or other alert, by way of non-limiting example. The firing mechanism 56 performance may thus be variable, such as by actuation of the locking mechanism 76, to vary delivery, such as based on different types of the deliverable 14/cassette 12.

The injector pen 16 may include software or firmware 80*a*, such as to control and execute the various functions of the injector pen 16 as discussed throughout, including reading of the cartridge identification, actuation of the UI/AM or locking mechanism, and communications with the base station and/or the gateway. Accordingly, the injector pen 16 may additionally include memory 80*b* for storage of these components, and/or processing capability 80*c*.

As referenced, the injector pen 16 communicates with at least the cartridge 12 and the gateway 100 at the base station 20. Thus, the injector pen 16 may include any of various communications hardware/antennas, such as NFC, Bluetooth, or WiFi, for example.

The base station 20 includes the communications gateway 100, an identification reader 82 and a charger 84 for the delivery device 16. The communications gateway 100 is capable of communicating with the injector pen 16, both when it is and is not placed in physical association with the base station 20, and with the hub 24 in the cloud 28. Thus, the pen 16 may or may not be physically associated with the base 20 in order to communicate. Moreover, wireless communication may be local as between the pen 16 and the base 20, or may be remote.

The communications gateway 100 may allow for two way communication with both the pen 16 and the hub 24, so as to enable uploading of data, and additionally downloading of data and information. By way of non-limiting example, operating system upgrades for the base station 20 or the injector pen 16 may be downloaded, such as via push or pull, from the hub 24, by way of example.

Accordingly, the base station 20 may include a plurality of antennas/readers, and the corresponding communications control software and processing 88. The plurality of antennas and reading capabilities 88 may include, but not be limited to, Bluetooth, Wifi, NFC, Ethernet, USB, NFC and cellular.

The charger 84 in the base station 20 charges the injector pen 16 upon association with the base station 20. As such, the base station 20 may include a pinned cradle, a USB port, or the like 84 to allow for delivery of power to the injector pen 16 upon association with the base station 20. Accordingly, the base station 20 may plug in to utility power 92, and may include power conversion such that the power delivered by the base station 20 is suitable to trickle charge the injector pen 16.

Of course, the base station 20 may additionally include a rechargeable battery 94. The battery 94 may provide that the base station 20 can carry out at least limited functionality, including some level of communications to the cloud hub 24 and charging of the injector pen 16, even in the event utility power 92 is lost or unavailable.

That is, in some instances, functionality provided at the base station 20 may vary, such as in the event of power loss. Thus, the base station 20 may include long term, short term, and batch memory capability 96. Thereby, data received at the base station 20 may be batched for later upload to the cloud hub 24 via the gateway 100, such as in order to limit power usage by the communications aspects during a loss of utility power 92, by way of example.

The base station may include one or more user interfaces (UI) and/or alert mechanisms (AM) 98. The UI/AM may be visual, audible, or tactile, such as a LCD, LEDs, speakers, or a buzzer. The UI/AM may receive user input, and may deliver alerts or instructions to the user/patient.

As referenced, the base station 20 includes a communications gateway 100. The injector pen 16 may communicate directly with an app 30 on a smart phone 32, but more preferably the injector pen 16 may communicate specifically with the gateway 100, and the gateway, in turn, may manage all communications with the smart phone app 30 and with the cloud hub 24.

Elderly and/or infirm users may struggle to use smart phone 32—so the gateway 100 may pull and may additionally store data from the injector pen 16 (such as for batch upload to the app and the hub) automatically. Processing by the gateway 100 of this pulled data, alone or in conjunction with data from the cloud hub 24, may allow for the triggering of alerts or instructions 110, provided on or to the phone, via text or email, or to the injector pen 16, and may allow for the providing of those alerts or instructions to either the patient or a caregiver, and/or to third party.

By way of example, instructions 110 may include use-instructions. For example, instructions 110 may comprise a certain sequence of elements of pen 16 lighting up in a certain order so as to provide a sequenced "user manual". Instructions or alerts 110 may additionally include audible aspects, such as may occur in conjunction with the lights at certain points on or around the pen 16 to as to provide similar sequenced use instructions.

By way of further non-limiting example, the gateway 100 may enable auto-replenishment. Between the gateway 100 and the hub 24, tracking may occur of the amount of deliverable 14 needed and the timing needed (as the prescription and proper usage information may be known from the injector pen and a secure patient account at the hub), and the amounts ordered and timing of orders, and can thereby automatically execute an auto-replenishment request.

For example, the sensing 112 discussed throughout (i.e., sensing of storage; sensing of dose dispensing; etc.), in conjunction with information from the hub 24 (i.e., prescribed total amount; prescribed daily dosage; etc.) may allow for the actuation of an auto-replenishment trigger at the hub 24. As used herein, an auto-replenishment may include an affirmative ordering of additional cartridges, an injector pen, a base station, and so on by or to a third party; an alert to a doctor that a [articular patient is in need of additional cartridges on or before a certain date; and/or an alert to a patient's account from the hub, such as to the patient's smart phone, that a new series of cartridges will be needed by or before a certain date.

Accordingly, software 120 associated with the hub (or, in a localized embodiment, with the gateway) may include replenishment algorithms 120*a*. Included within the replenishment algorithms 120*a* may be the ability to define and communicate the need for replenishment. Accordingly, an autoreplenishment may be triggered by a need for auto replenishment as set by the patient, a pharmacy, a doctor, or a brand, or may occur on fixed time intervals, such as may be calculated for a particular medication based on the date a prescription is filled.

The presence of controls and communications in the base station gateway, as discussed throughout, provides distinct advantages. For example, the presence of substantial electronics in the base station avoids the need for component miniaturization that would occur if the electronics were largely present in the injector pen. This additionally provides enhanced simplicity of use and lowers the cost per dose of the deliverable.

Yet further, as the cartridge may be single use, and the injector may wear out faster due to the repeated high stress of delivering doses (i.e., 1-3 years), a heavier reliance on the more robust base station may prolong usable system life. For example, the inclusion of the most expensive electronics in the longest surviving, least used system component, i.e., the base station, limits the need for replacement of the more expensive system aspects to a longer timeframe, such as once every 5-7 years.

Figure 2A:
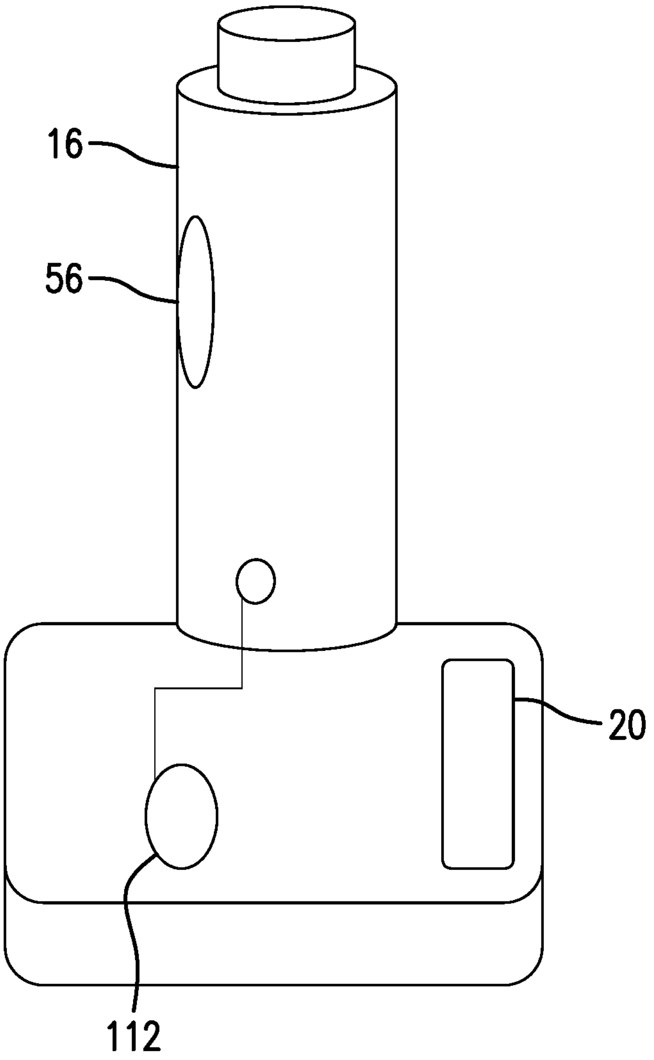
FIG. 2*a* is an illustration of aspects of the embodiments.
Figure 2B:
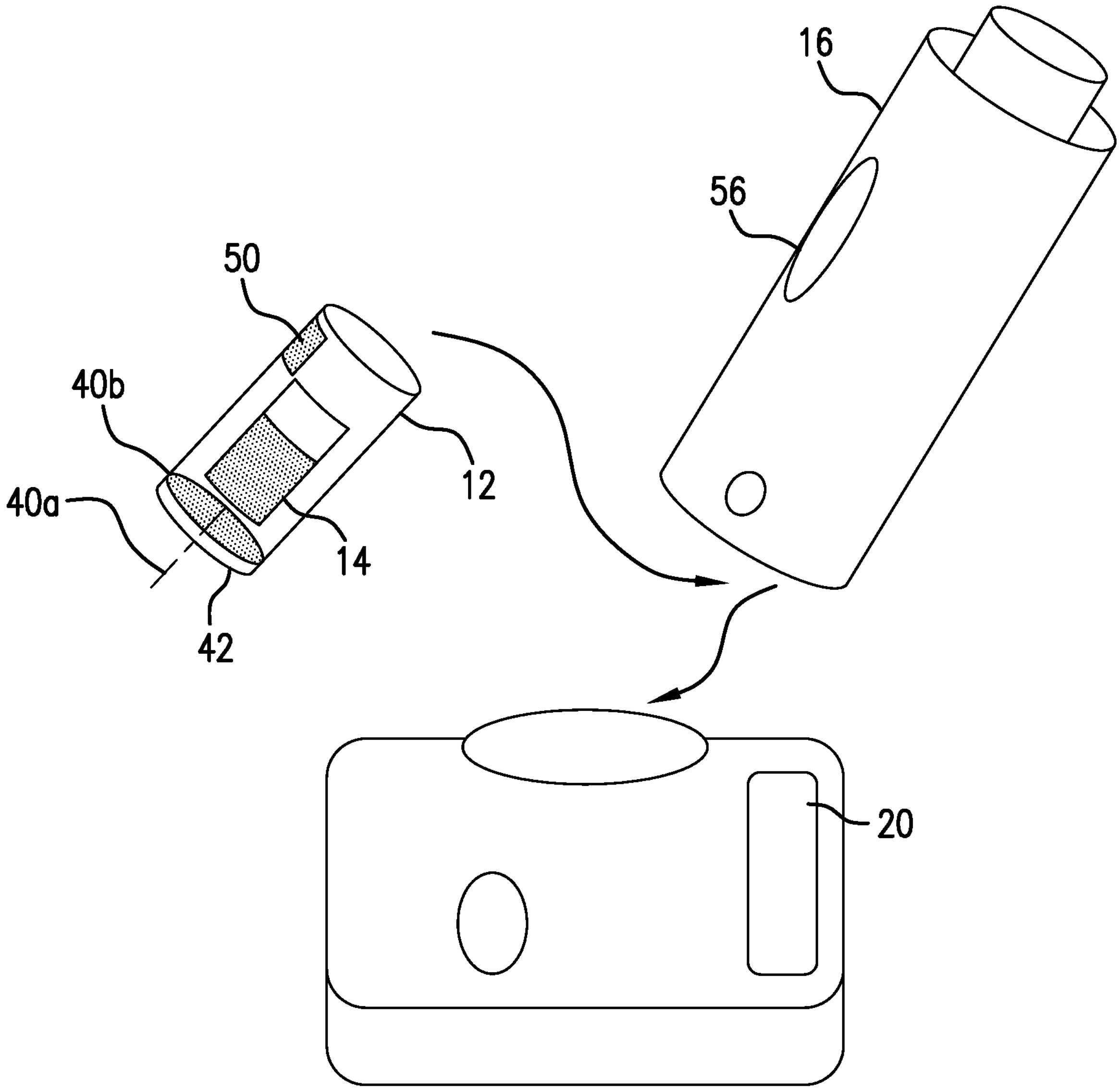
FIG. 2*b* is an illustration of aspects of the embodiments.
Figure 2C:
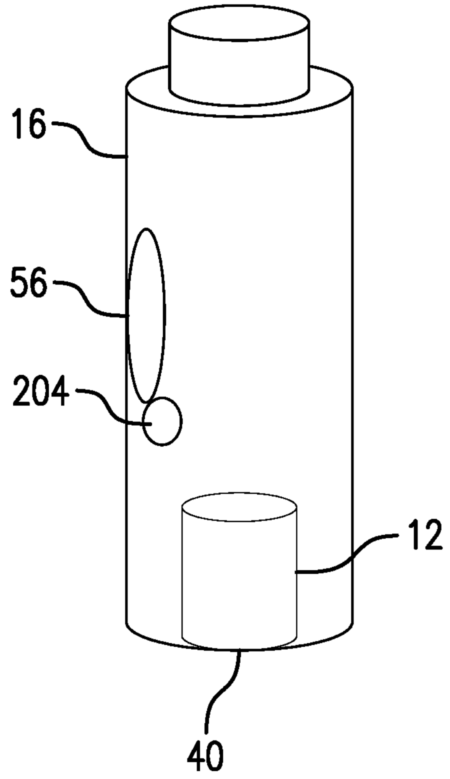
FIG. 2*c* is an illustration of aspects of the embodiments.

As illustrated in FIG. 2, the pen 16 is stored in and charged by the base 20. As such, the base 20 may include charging components 200 (i.e., power adaptor, AC/DC conversion, trickle charge output). During association with the base 20, the pen 16 may also upload information via wire that is not wirelessly provided to the gateway 100, such as via the power connection cable to the base or via another hardwired output from the pen to the base.

The cassette 12 is loaded into the charged injector pen 16. The pen 16 does any necessary sensing and, if injection is acceptable, fires the firing mechanism 56 to discharge the deliverable 14 from the cassette 12 through the needle 40 into the patient at the appropriate time. The appropriate time and placement may be manually indicated by the patient, such as by actuation of a button 204 on the pen 16, or may be sensed by sensing in-board the pen 16.

Once discharged, the cassette 12 is discarded. The pen 16 may then be returned to the base 20, such as for uploading of information to the base 20 from the pen 16, and/or to allow for charging of the pen 16 via the power passing through or stemming from the base station 20. Of note, the pen 16 may receive the charge from the base 20 via any means known to the skilled artisan, including but not limited to contact charging, plug-in charging, inductive charging, and so on.

Figure 3:
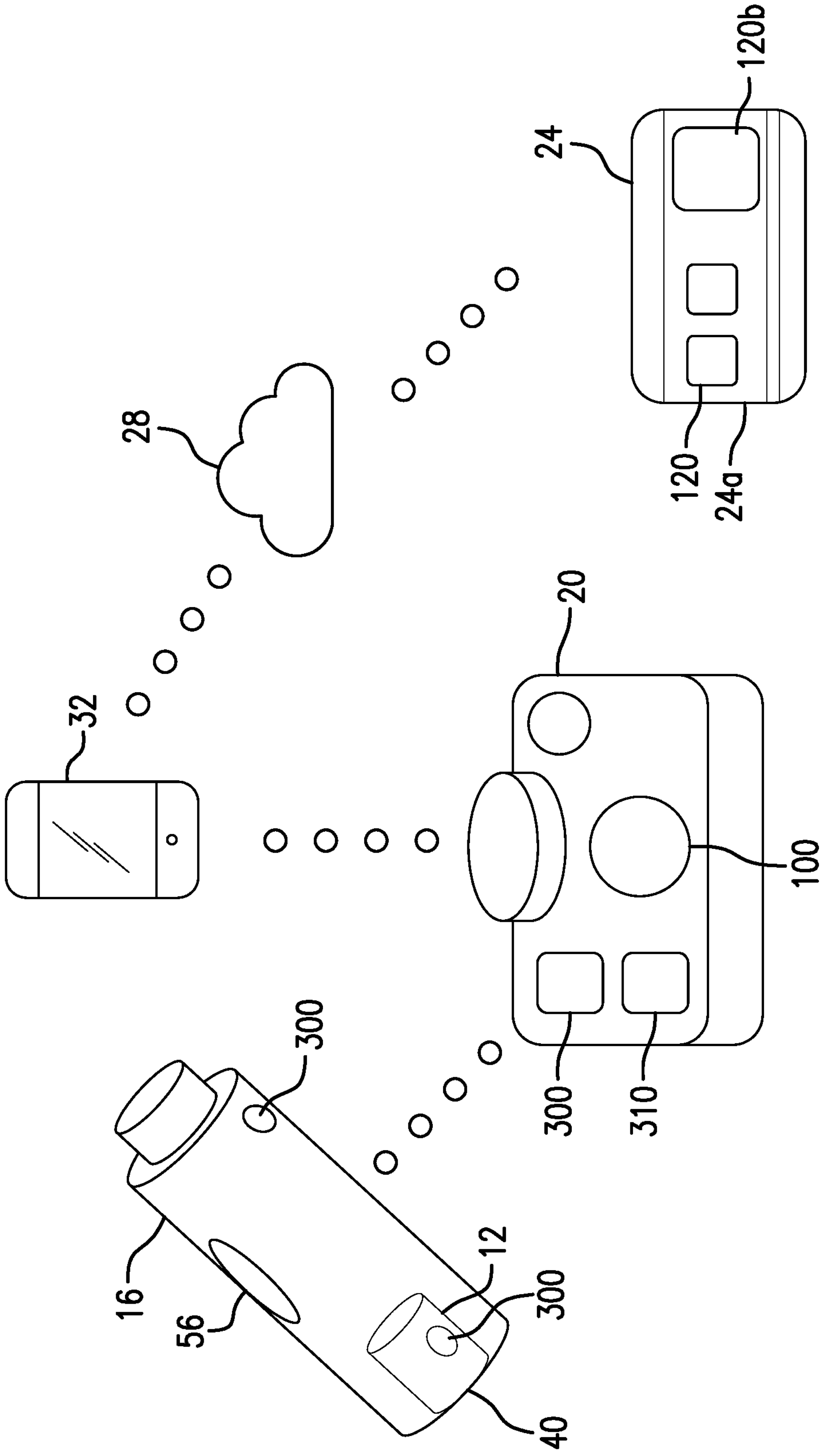
FIG. 3 is an illustration of aspects of the embodiments.

As illustrated in FIG. 3, the pen 16, the cassette 12, and/or the gateway 100 may each include electronic identification 300. For example, each may include a RFID tag and/or a near field communications (NFC) tag. Thereby, the patient may be verified, the deliverable may be verified, and any variations in drug delivery via the firing mechanism 56 or necessary lock-outs may be effectuated, all based on the identification trial 300.

Communications, including identification and/or synchronization, may occur wirelessly from the pen 16 to the base 20, or may occur via wire upon association of the pen 16 into the base 20, such as during recharging, as referenced above. Wireless communication from the pen 16 to the base 20 may, for example, occur via Bluetooth. Communication from the pen 16 once in the base 20 may occur from the pen 16 using, for example, wire and/or NFC.

The gateway 100 of the base station 20 may, in turn, communicate with the cloud hub 24 and/or directly with a local smartphone 32 via wired or wireless methods, and most preferably by wireless methods. For example, the gateway 100 may include communications capabilities 302 to use Bluetooth to communicate with the pen 16 and/or any nearby communications center; and/or to use WiFi capabilities to use a nearby LAN; and/or to use cellular functionality in order to communicate to the cloud hub 24 over the cellular/PSTN networks.

The gateway 100 may be enabled to communicate to a variety of destinations, such as to a "home base" in the cloud, and/or to a nearby smartphone having proper secured identification and a suitable "app". Alternatively, in the case of a communications breakdown, the gateway 100 may include storage capabilities 310 in order to hold some sub-set of obtained data until an upload can occur.

Figure 4:
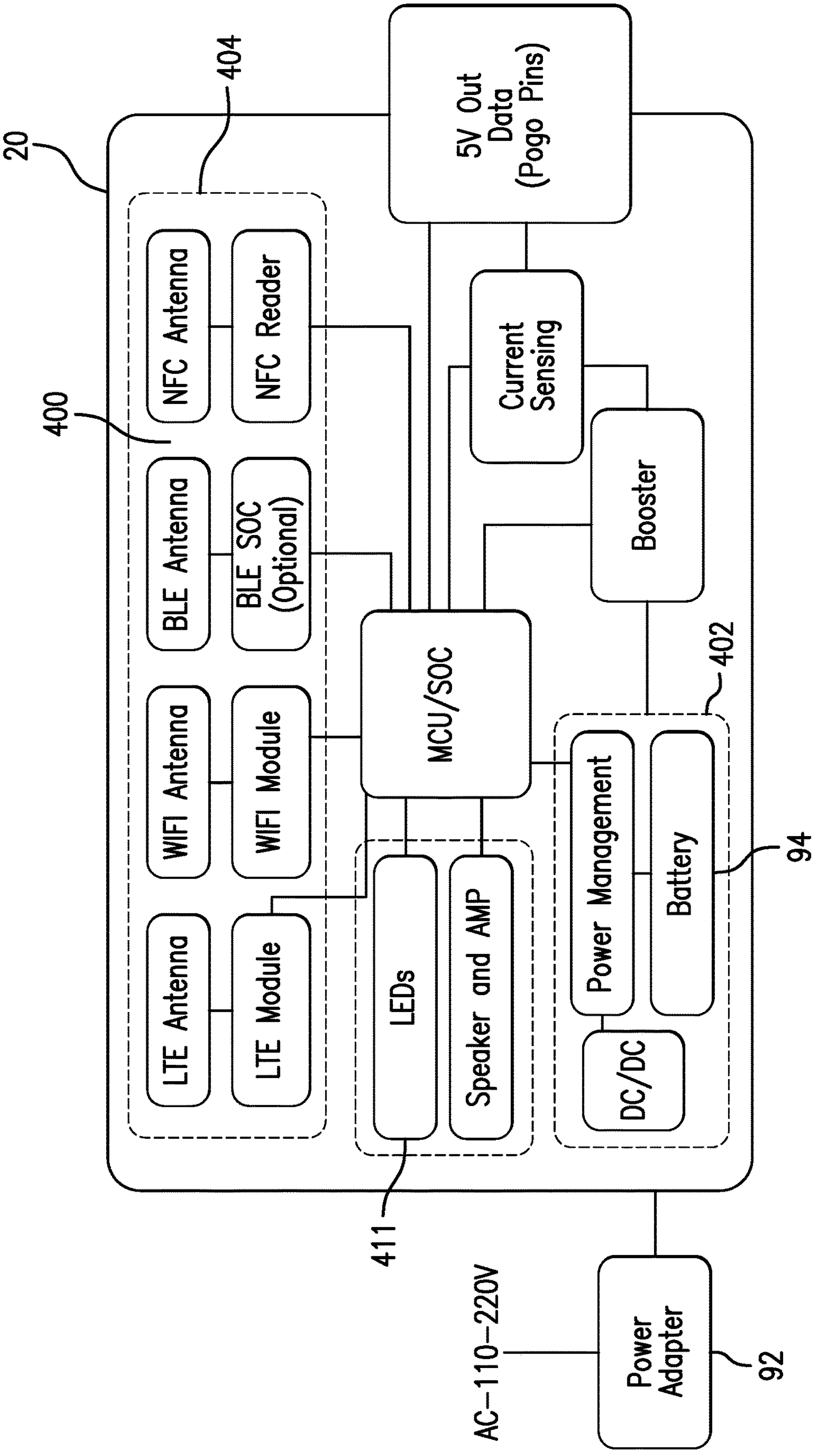
FIG. 4 is an illustration of aspects of the embodiments.

FIG. 4 illustrates the base station architecture 400 with particularity. The base station 20 includes charging capabilities 402 and communication capabilities 404. Thus, the base station 20 may include receipt of utility power 92. As such, the base station 20 may "plug in", and may have the requisite voltage and power conversions in order to use the supplied utility power.

The base station 20 may additionally have a battery backup 94, such as for supplied power in instances of loss of power. Needless to say, drug delivery to a patient, and accumulation of delivery data, must occur even in the event of lack of utility power 92.

The base station 20 may thus also provide a power-savings mode, such as wherein data is batched and stored when battery power 94 is being used. In this mode, the base station 20 may thereby avoid drawing on battery power 94 for wireless communications, by stalling uploads/downloads until utility power is restored.

As referenced throughout, the base station 20 includes capabilities to communicate with the patient or a caregiver 411. The base station may thus include a LCD screen, a touch pad, LEDs, an audio announcement/audio card with speakers, and so on. These communications aspects 411 may communicate, directly to the caregiver or patient, instructions or alerts, for example, and these communications may be in place of or in addition to the communications with a smart phone 32 or with the hub 24 as discussed throughout.

These patient communication features 411 may be in addition to the various communications capabilities 404 discussed throughout. For example, the base station may communicate via wire to the injector pen when the pen is cradled in the base station; the base station may communicate via wire to the cloud hub/internet; the base station may communicate via NFC to the pen when the pen is in or near the base; the base station may communicate via Bluetooth to the pen when the injector pen is not in the base; the base station may communicate via Bluetooth to the hub/cloud; the base may communicate via WiFi to the pen and/or to the cloud hub; and the base station may communicate via cellular, such as to the cloud hub. Of course, power charging of and communication with the injector pen may overlap, such as occurring via a 5V DC charging port/pin port, a USB plug-in port, or the like.

Both the pen and the base station may thus be "smart", as discussed throughout, i.e., may communicate directly with an app, for example. However, for the sake of data integrity, and to avoid data redundancy, and absent a power outage, the master data communication may be from the base station to the cloud hub. The hub may then push data to the app, such as via a cellular connection, and the hub may track cartridge use for propriety and compliance of use, for auto-replenishment, and so on, for example. Thus, use of the hub-to-base connection as the master, or primary, communication mode improves data integrity and lowers data maintenance.

Figure 5:
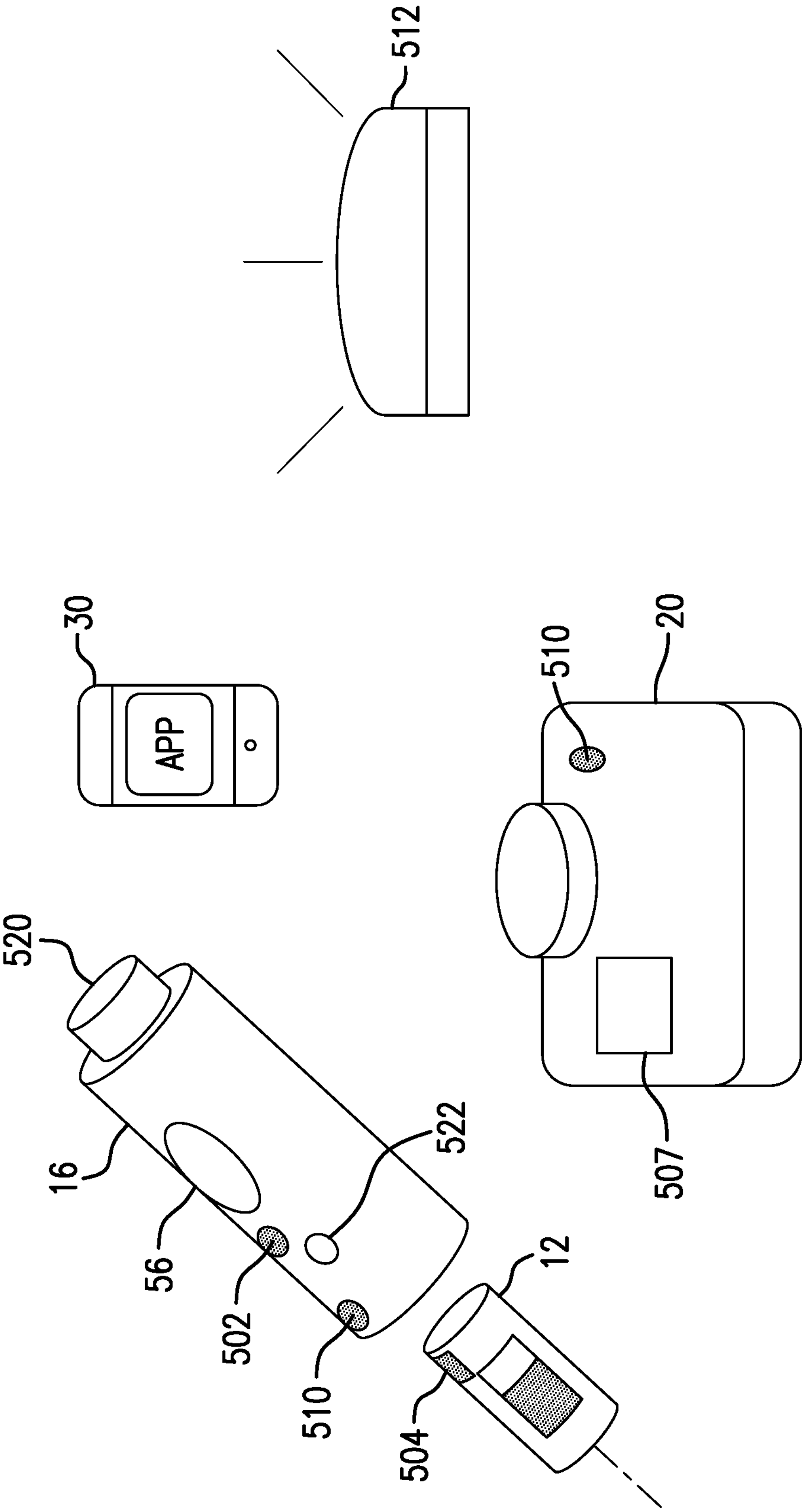
FIG. 5 is an illustration of aspects of the embodiments.

FIG. 5 illustrates that each pen 16 may have a unique ID (RFID and/or NFC, for example) 502. Each cassette 12 may have a unique ID 504 (which may identify the drug, the batch code, the dosage, the prescription number, etc.). The pen 16 may then either "check" the cassette ID 504 itself, or may pass the cassette ID 504 to the gateway 100 in the base station 20 to check. Or, the pen 16 may pass the cartridge ID 504 to the smartphone app 30 to check, such as to ensure, record, and/or identify aspects of the dose delivery event. Aspects identified may include the patient, the dosage, the drug being delivered, the compliance with recommended usage of the drug, the compliance with prescription aspects, the recall of a certain drug or cartridge, the propriety of the time and day of the delivery of that drug, and so on.

The identified aspects may be used to, for example, generate alerts 510. Identification of the wrong drug, the wrong dose, an expired drug, a broken cold chain, a gray-coded dose, a falsified serial numbered dose, a drug recall, a missed dose, or an incorrect delivery attempt, for example, may lead to an alert. Some of these alerts 510 may be based solely upon the identification, and some may be based upon identification in conjunction with a secondary sensing (such as a proximity sensing, a temperature sensor, a pressure sensor, and so on).

Alerts 510 may be audible, visual, tactile (such as shaking or buzzing); may use surrounding mechanisms 512, such as a synch to Alexa or Google Home, such as to blink lights in the house or sound an alarm; or may be triggering mechanisms for mechanical or electro-mechanical actuation, such as locking of the firing mechanism 56 of the injector pen 16 as discussed above. Of course, the foregoing synchronizations are provided by way of example only, and the skilled artisan will thus appreciate that the embodiments may operate and/or synchronize with any known platforms and/or operating systems, such as iOS-based systems, Android-based systems, and the like. By way of non-limiting example, certain drugs may require a "cold chain" of controlled temperature, or may necessitate being placed at room temperature for a certain timeframe, such as 30 minutes, before delivery into a patient.

In each such case, the injector pen may "smart sense" the cassette and its temperature, and may be provided with information from or through the gateway regarding chain of custody and/or historical temperature check events regarding the cassette. If a violation is sensed in the cold chain, or the chain of custody, or in the relative distance of the cartridge from room temperature, by way of non-limiting example, an alert may occur, and such an alert may include a locking of the pen's firing mechanism 56 via the locking mechanism discussed above. Moreover, the smart nature of the pen 16 may allow for alternative alarm activity, such as locking the firing mechanism 56 for a certain timeframe until room temperature is reached by the cartridge per the sensors, or simply for a certain time period.

As set forth herein, "identification" may include "de-identification" in certain embodiments. For example, the patient identification may be de-identified from the remainder of the dose delivery-record. This may be necessary in certain embodiments for HIPAA compliance purposes, for example. By way of example, certain aspects of HIPAA carry various requirements for maintaining patient identification in association with other data in computing memory, and on the security levels required for data maintenance.

Moreover, certain information may be de-identified for certain purposes within the disclosed system, but identified in other aspects of the system. By way of example, the patient identification may be securely maintained at the base station 20 or at the cloud hub 24 only, and the patient may be de-identified from the delivery record in all other regards, i.e., at the pen or at the base station. Thereby, certain data may be maintained, and/or certain other data may be anonymized, such as for subsequent aggregation purposes as discussed herein.

Of course, to avoid the need to de-identify, the injector pen 16 may include an agnostic locking mechanism 522, as may the base station 20, such as may be tied to a bio-sensor 520. That is, the identification of the patient may not be stored, maintained, or uploaded, but the bio-sensor may "lock out" anyone who does not match a previously input bio-identification. By way of example, an injector pen 16, which may be an injector pen dedicated to injecting a particular drug, or dedicated to a particular user, such as via its respective firmware programming, may include a finger/thumb print, eye, or facial identification capability 520. Accordingly, if the bio-sensor 520 "sees" a properly matching identification, it may allow for delivery of the drug. If the sensing "sees" is a mismatch, then the injector pen may lock.

The alert mechanisms 510 on the injector pen 16 may also be used to provide instructions or guidance on dosing, for example. The most difficult time to comply with a drug delivery protocol is early in the protocol, as the patient is unsure of how to use the delivery mechanism and/or is unclear on how to take the drug. As such, a new user/drug may be recognized upon insertion of the cassette 12, and alert mechanisms 510 may be used to provide a digital guide for delivery. By way of example, features of the pen may light up in a certain order, or audible sounds may emanate from speakers at different points on the device and in a particular order.

Figure 6:
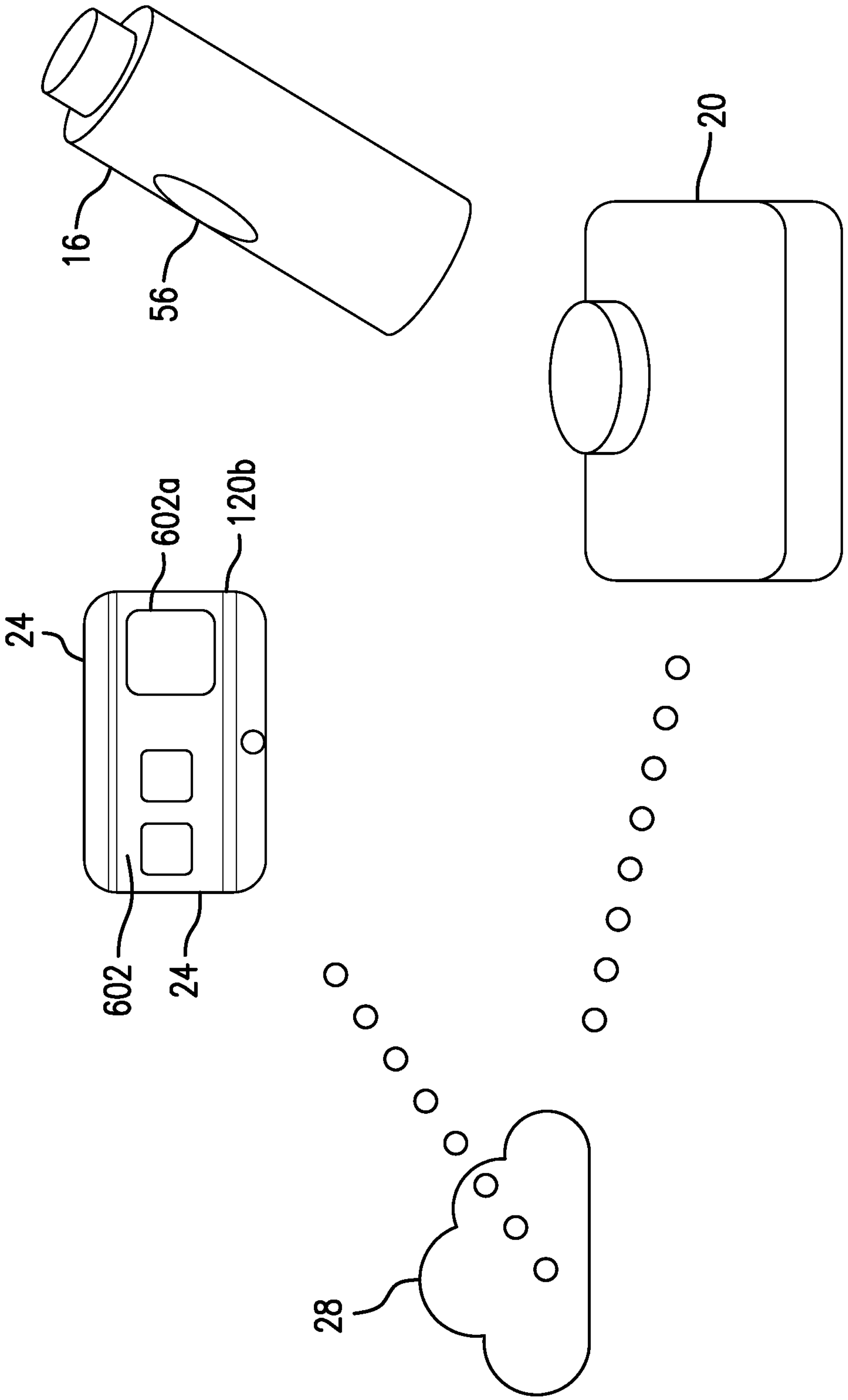
FIG. 6 is an illustration of aspects of the embodiments.

Thus, and as illustrated in FIG. 6, the embodiments allow for a voluminous accumulation of "big data" 602 at the hub 24 in the cloud. This data 602 may be anonymized as to the patient or user, such as per HIPAA protocols. This data 602 may include full tracking **602*a* of drug batches, from laboratory creation through dose delivery, and at all points in between. Tracking 602*a*** may include temperature, geo-location, propriety of dose delivery, and so on.

This information 602 may be useful for auto-replenishment/reorder, as referenced above. The information 602 may additionally be of use for pharmaceutical companies, such as to track use by location, or for comparative sales success data as compared with generic drugs.

Figure 7:
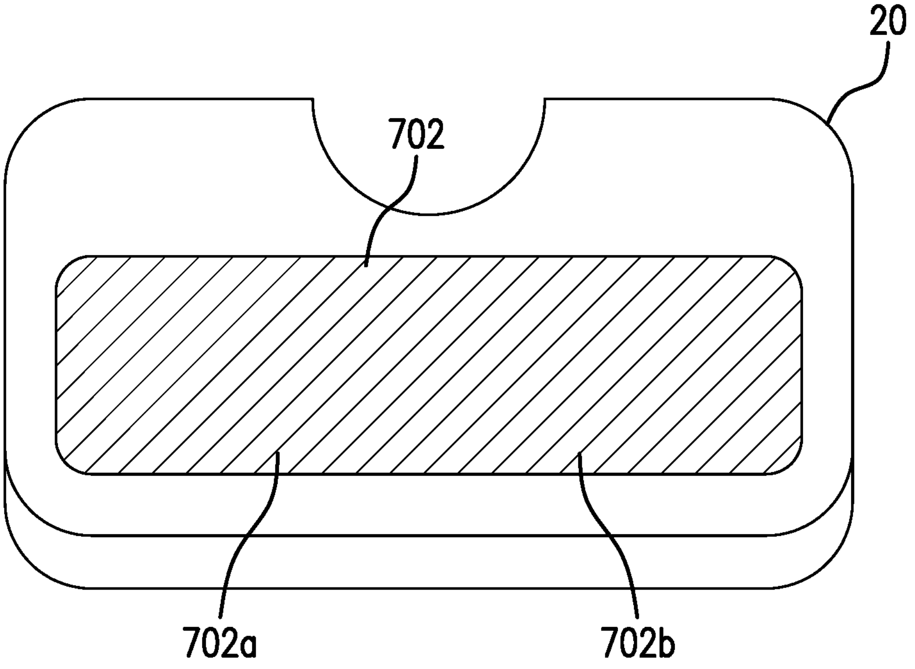
FIG. 7 is an illustration of aspects of the embodiments.

As illustrated in FIG. 7, the base station 20 may also include storage area 702 for one or more cartridges 12. This storage 702 may include, for example, temperature-controlled storage wherein the temperature is controlled and monitored by the gateway 100. Accordingly, cold custody and chain of custody may readily be monitored and tracked in such embodiments. Of course, such closed-system tracking may also improve data 602 to enable the other features disclosed herein, such as auto-replenishment.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A medication delivery system, comprising:

a powered mobile injector pen capable of receiving a cartridge having a deliverable therein, and of delivering the deliverable to a patient;

a base station physically separate from the injector pen, suitable to receive communications from, and to provide an electrical charge and recharge to, the powered injector pen, and comprising a communications gateway; and a remote communications hub capable of exchanging wireless communications with the communications gateway, wherein the powered mobile injector pen is physically detached from the base station when delivering the deliverable, wherein the power mobile injector pen comprises an electronic reader, a firing mechanism and a locking mechanism that is separate from the electronic reader, wherein each of the powered mobile injector pen and the cartridge comprise an electronic identifier, wherein the base station is configured to read the electronic identifier of the powered mobile injector pen, and the electronic reader of the powered mobile injector pen is configured to read the electronic identifier of the cartridge, and wherein the locking mechanism mechanically prevents actuation of the firing mechanism based on information read from the electronic identifiers of the powered mobile injector pen and the cartridge.

2. The system of claim 1, further comprising an app on a mobile device that is capable of wireless communication with the powered injector pen, the base station, and the hub.

3. The system of claim 1, wherein the deliverable is medication.

4. The system of claim 1, wherein the firing mechanism is electro-mechanical.

5. The system of claim 1, wherein the firing mechanism fires a needle associated with the cartridge.

6. The system of claim 1, wherein the firing mechanism fires a needle associated with the injector pen.

7. The system of claim 1, wherein the locking mechanism prevents inappropriate delivery of the deliverable.

8. The system of claim 7, wherein the inappropriate delivery comprises an incorrect patient.

9. The system of claim 7, wherein the inappropriate delivery comprises an incorrect deliverable.

10. The system of claim 7, wherein the inappropriate delivery comprises a non-compliant delivery.

11. The system of claim 1, wherein the electronic identifiers of the powered mobile injector pen and the cartridge comprise at least one of a RFID tag, a bar code, a QR code, a near field communications (NFC) tag, and an electronic signature.

12. The system of claim 1, wherein at least one of a user interface of the powered injector pen and a user interface of the base station is visual, audible, or tactile.

13. The system of claim 1, wherein at least one of an alert mechanism of the powered injector pen and an alert mechanism of the base station is visual, audible, or tactile.

14. The system of claim 13, wherein at least one of the alert mechanisms comprise a series of use instructions for the cartridge.

15. The system of claim 13, wherein at least one of the alert mechanisms is indicative of an attempted inappropriate delivery of the deliverable.

16. The system of claim 15, wherein the inappropriate delivery comprises an incorrect deliverable.

17. The system of claim 1, the base station further comprising a temperature-controlled storage area for one or more cartridges.

* * * * *